US010777319B2

(12) United States Patent
Shapley et al.

(10) Patent No.: US 10,777,319 B2
(45) Date of Patent: *Sep. 15, 2020

(54) THERAPEUTIC PRODUCT DELIVERY SYSTEM AND METHOD OF PAIRING

(71) Applicant: INSULET NETHERLANDS B.V., Schiphol (NL)

(72) Inventors: Julian Shapley, Swansea (GB); Matthew Powell, Swansea (GB); Mark Jones, Swansea (GB)

(73) Assignee: INSULET NETHERLANDS B.V., Schiphol (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/592,679

(22) Filed: Oct. 3, 2019

(65) Prior Publication Data

US 2020/0105408 A1    Apr. 2, 2020

Related U.S. Application Data

(63) Continuation of application No. 15/114,843, filed as application No. PCT/GB2015/050248 on Jan. 30, 2015, now Pat. No. 10,438,696.

(30) Foreign Application Priority Data

Jan. 30, 2014    (GB) .................................. 1401591.1

(51) Int. Cl.
*G16H 40/63*    (2018.01)
*A61M 5/142*    (2006.01)
(Continued)

(52) U.S. Cl.
CPC ........ *G16H 40/63* (2018.01); *A61M 5/14244* (2013.01); *A61M 5/1723* (2013.01);
(Continued)

(58) Field of Classification Search
CPC ........... A61M 5/14244; A61M 5/1723; H04W 48/16; H04W 76/40; H04L 63/06; H04L 63/0428
See application file for complete search history.

(56) References Cited

U.S. PATENT DOCUMENTS 3,631,847 A    1/1972    Hobbs
3,812,843 A    5/1974    Wootten et al.
(Continued)

FOREIGN PATENT DOCUMENTS

AU    2015301146 A1    3/2017
CN    1297140 A    5/2001
(Continued)

OTHER PUBLICATIONS

US 5,954,699 A, 09/1999, Jost et al. (withdrawn)
(Continued)

*Primary Examiner* — Nabil H Syed

(57) ABSTRACT

A method of pairing a therapeutic product delivery device to a handset is described. The handset is restricted to controlling only delivery devices which it is paired with. The method comprises the steps of: at the delivery device, setting, in response to the delivery device being connected to a charging device, a pairing indicator indicating that the delivery device is available for pairing, and broadcasting the pairing indicator using a radio transceiver; at the handset, discovering the delivery device based on the broadcast pairing indicator; and pairing the discovered delivery device and the handset together. By limiting the handset to pairing with devices which are broadcasting a pairing indicator, and by limiting the setting and/or broadcast of the pairing indicator to when the delivery device is connected to a (Continued)

charging device, the risk of accidentally pairing the wrong delivery device (for example someone else's) to the handset is greatly reduced.

15 Claims, 6 Drawing Sheets

(51) Int. Cl.
| | | |
|---|---|---|
| *H04W 76/40* | (2018.01) | |
| *G16H 40/40* | (2018.01) | |
| *A61M 5/172* | (2006.01) | |
| *H04B 5/00* | (2006.01) | |
| *H04L 29/06* | (2006.01) | |
| *H04W 48/16* | (2009.01) | |

(52) U.S. Cl.
CPC ........... *G16H 40/40* (2018.01); *H04B 5/0031* (2013.01); *H04L 63/0428* (2013.01); *H04L 63/06* (2013.01); *H04W 48/16* (2013.01); *H04W 76/40* (2018.02); *A61M 2205/14* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/505* (2013.01); *A61M 2205/8206* (2013.01); *A61M 2205/8237* (2013.01); *A61M 2209/086* (2013.01); *A61M 2230/201* (2013.01)

(56) References Cited

U.S. PATENT DOCUMENTS

| | | |
|---|---|---|
| 3,841,328 A | 10/1974 | Jensen |
| 3,963,380 A | 6/1976 | Thomas, Jr. et al. |
| 4,151,845 A | 5/1979 | Clemens |
| 4,373,527 A | 2/1983 | Fischell |
| 4,469,481 A | 9/1984 | Kobayashi |
| 4,475,901 A | 10/1984 | Kraegen et al. |
| 4,529,401 A | 7/1985 | Leslie et al. |
| 4,559,033 A | 12/1985 | Stephen et al. |
| 4,559,037 A | 12/1985 | Franetzki et al. |
| 4,624,661 A | 11/1986 | Arimond |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,886,499 A | 12/1989 | Cirelli et al. |
| 4,994,047 A | 2/1991 | Walker et al. |
| 5,109,850 A | 5/1992 | Blanco et al. |
| 5,125,415 A | 6/1992 | Bell |
| 5,153,827 A | 10/1992 | Coutre et al. |
| 5,176,662 A | 1/1993 | Bartholomew et al. |
| 5,178,609 A | 1/1993 | Ishikawa |
| 5,232,439 A | 8/1993 | Campbell et al. |
| 5,244,463 A | 9/1993 | Cordner, Jr. et al. |
| 5,257,980 A | 11/1993 | Van Antwerp et al. |
| 5,281,808 A | 1/1994 | Kunkel |
| 5,342,298 A | 8/1994 | Michaels et al. |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,507,288 A | 4/1996 | Bocker et al. |
| 5,533,389 A | 7/1996 | Kamen et al. |
| 5,584,813 A | 12/1996 | Livingston et al. |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Komerup |
| 5,693,018 A | 12/1997 | Kriesel et al. |
| 5,716,343 A | 2/1998 | Kriesel et al. |
| 5,741,228 A | 4/1998 | Lambrecht et al. |
| 5,755,682 A | 5/1998 | Knudson et al. |
| 5,800,405 A | 9/1998 | McPhee |
| 5,800,420 A | 9/1998 | Gross et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,931,814 A | 8/1999 | Alex et al. |
| 5,935,099 A | 8/1999 | Peterson et al. |
| 5,993,423 A | 11/1999 | Choi |
| 5,997,501 A | 12/1999 | Gross et al. |
| 6,024,539 A | 2/2000 | Blomquist |
| 6,050,978 A | 4/2000 | Orr et al. |
| 6,071,292 A | 6/2000 | Makower et al. |
| 6,090,092 A | 7/2000 | Fowles et al. |
| 6,126,637 A | 10/2000 | Kriesel et al. |
| 6,200,338 B1 | 3/2001 | Solomon et al. |
| 6,244,776 B1 | 6/2001 | Wiley |
| 6,309,370 B1 | 10/2001 | Haim et al. |
| 6,475,196 B1 | 11/2002 | Vachon |
| 6,477,901 B1 | 11/2002 | Tadigadapa et al. |
| 6,544,212 B2 | 4/2003 | Galley et al. |
| 6,554,798 B1 | 4/2003 | Mann et al. |
| 6,569,125 B2 | 5/2003 | Jepson et al. |
| 6,572,542 B1 | 6/2003 | Houben et al. |
| 6,699,221 B2 | 3/2004 | Vaillancourt |
| 6,740,059 B2 | 5/2004 | Flaherty |
| 7,008,404 B2 | 3/2006 | Nakajima |
| 7,018,360 B2 | 3/2006 | Flaherty et al. |
| 7,025,744 B2 | 4/2006 | Utterberg et al. |
| 7,128,727 B2 | 10/2006 | Flaherty et al. |
| 7,144,384 B2 | 12/2006 | Gorman et al. |
| 7,303,549 B2 | 12/2007 | Flaherty et al. |
| 7,651,845 B2 | 1/2010 | Doyle, III et al. |
| 7,918,825 B2 | 4/2011 | OConnor et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatlield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,579,456 B2 | 2/2017 | Budiman et al. |
| 9,907,515 B2 | 3/2018 | Doyle, III et al. |
| 9,984,773 B2 | 5/2018 | Gondhalekar et al. |
| 10,248,839 B2 | 4/2019 | Levy et al. |
| 2001/0034023 A1 | 10/2001 | Stanton, Jr. et al. |
| 2001/0034502 A1 | 10/2001 | Moberg et al. |
| 2001/0053895 A1 | 12/2001 | Vaillancourt |
| 2002/0010423 A1 | 1/2002 | Gross et al. |
| 2002/0016568 A1 | 2/2002 | Lebel et al. |
| 2002/0123740 A1 | 9/2002 | Flaherty et al. |
| 2002/0161288 A1 | 10/2002 | Shin et al. |
| 2003/0060692 A1 | 3/2003 | Ruchti et al. |
| 2003/0135388 A1 | 7/2003 | Martucci et al. |
| 2003/0163097 A1 | 8/2003 | Fleury et al. |
| 2003/0212379 A1 | 11/2003 | Bylund et al. |
| 2003/0220605 A1 | 11/2003 | Bowman, Jr. et al. |
| 2004/0010207 A1 | 1/2004 | Flaherty et al. |
| 2004/0051368 A1 | 3/2004 | Caputo et al. |
| 2004/0116847 A1 | 6/2004 | Wall |
| 2004/0133166 A1 | 7/2004 | Moberg et al. |
| 2004/0171983 A1 | 9/2004 | Sparks et al. |
| 2005/0020980 A1 | 1/2005 | Inoue et al. |
| 2005/0075624 A1 | 4/2005 | Miesel |
| 2005/0203461 A1 | 9/2005 | Flaherty et al. |
| 2005/0238507 A1 | 10/2005 | Dilanni et al. |
| 2005/0272640 A1 | 12/2005 | Doyle, III et al. |
| 2005/0277912 A1 | 12/2005 | John |
| 2006/0134323 A1 | 6/2006 | OBrien |
| 2006/0173406 A1 | 8/2006 | Hayes et al. |
| 2006/0204535 A1 | 9/2006 | Johnson |
| 2006/0253085 A1 | 11/2006 | Geismar et al. |

(56) References Cited

U.S. PATENT DOCUMENTS

| | | |
|---|---|---|
| 2006/0270983 A1 | 11/2006 | Lord et al. |
| 2006/0282290 A1 | 12/2006 | Flaherty et al. |
| 2007/0118405 A1 | 5/2007 | Campbell et al. |
| 2007/0129690 A1 | 6/2007 | Rosenblatt et al. |
| 2007/0249007 A1 | 10/2007 | Rosero |
| 2007/0282269 A1 | 12/2007 | Carter et al. |
| 2008/0033272 A1 | 2/2008 | Gough et al. |
| 2008/0065050 A1 | 3/2008 | Sparks et al. |
| 2008/0078400 A1 | 4/2008 | Martens et al. |
| 2008/0132880 A1 | 6/2008 | Buchman |
| 2008/0206067 A1 | 8/2008 | De Corral et al. |
| 2008/0269714 A1 | 10/2008 | Mastrototaro et al. |
| 2008/0287906 A1 | 11/2008 | Burkholz et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0318791 A1 | 12/2009 | Kaastrup |
| 2010/0057042 A1 | 3/2010 | Hayter |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2012/0010594 A1 | 1/2012 | Holt et al. |
| 2012/0053556 A1 | 3/2012 | Lee |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0232520 A1 | 9/2012 | Sloan et al. |
| 2012/0282111 A1 | 11/2012 | Nip et al. |
| 2012/0295550 A1 | 11/2012 | Wilson et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0261406 A1 | 10/2013 | Rebec et al. |
| 2013/0317753 A1 | 11/2013 | Kamen et al. |
| 2013/0338576 A1 | 12/2013 | OConnor et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0278123 A1 | 9/2014 | Prodhom et al. |
| 2014/0316379 A1 | 10/2014 | Sonderegger et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0213217 A1 | 7/2015 | Amarasingham et al. |
| 2015/0265767 A1 | 9/2015 | Vazquez et al. |
| 2015/0306314 A1 | 10/2015 | Doyle et al. |
| 2016/0015891 A1 | 1/2016 | Papiorek |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0256087 A1 | 9/2016 | Doyle et al. |
| 2016/0287512 A1 | 10/2016 | Cooper et al. |
| 2016/0331310 A1 | 11/2016 | Kovatchev |
| 2017/0143899 A1 | 5/2017 | Gondhalekar et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2018/0036495 A1 | 2/2018 | Searle et al. |
| 2018/0204636 A1 | 7/2018 | Edwards et al. |
| 2018/0277253 A1 | 9/2018 | Gondhalekar et al. |
| 2018/0342317 A1 | 11/2018 | Skirble et al. |

FOREIGN PATENT DOCUMENTS

| | | |
|---|---|---|
| EP | 0341049 A2 | 11/1989 |
| EP | 0496305 A2 | 7/1992 |
| EP | 0801578 B1 | 7/2006 |
| EP | 2397181 A1 | 12/2011 |
| EP | 2830499 A1 | 2/2015 |
| EP | 2943149 A1 | 11/2015 |
| EP | 3177344 A1 | 6/2017 |
| EP | 3314548 A1 | 5/2018 |
| JP | 2004283378 A | 10/2004 |
| WO | 9800193 A1 | 1/1998 |
| WO | 9956803 A1 | 11/1999 |
| WO | 0030705 A1 | 6/2000 |
| WO | 0172354 A2 | 10/2001 |
| WO | 2002015954 A1 | 2/2002 |
| WO | 2005113036 A1 | 12/2005 |
| WO | 2006053007 A2 | 5/2006 |
| WO | 2007064835 A2 | 6/2007 |
| WO | 2008024810 A2 | 2/2008 |
| WO | 2008133702 A1 | 11/2008 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 20130149186 A1 | 10/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015061493 A1 | 4/2015 |
| WO | 2015073211 A1 | 5/2015 |
| WO | 2015081337 A2 | 6/2015 |
| WO | 2016022650 A1 | 2/2016 |
| WO | 2016141082 A1 | 9/2016 |
| WO | 2017004278 A1 | 1/2017 |
| WO | 2017205816 A1 | 11/2017 |

OTHER PUBLICATIONS

Anonymous: "Artificial pancreas—Wikipedia", Mar. 13, 2018 (Mar. 13, 2018), XP055603712, Retrieved from the Internet:URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinon for International application No. PCT/US17/53262, dated Dec. 13, 2017 8 pages.

Van Heusden, K. et al., "Control-Relevant Models for Glucose Control using a Priori Patient Characteristics", IEEE Transactions

(56) References Cited

OTHER PUBLICATIONS on Biomedical Engineering, vol. 59, No. 7, (Jul. 1, 2012) pp. 1839-1849.
Doyle III, et al., "Run-to-Run Control Strategy for Diabetes Management." Paper presented at 23rd Annual International Conference of the IEEE Engineering in Medicine and Biology Society, Istanbul, Turkey. (Oct. 2001).
Bequette, B.W., and Desemone, J., "Intelligent Dosing Systems": Need for Design and Analysis Based on Control Theory, Diabetes Technology and Therapeutics 9(6): 868-873 (2004).
Parker, R.S., et al., "A Model-Based Agorithm for Blood Gucose Control in Type 1 Diabetic Patients." IEEE Transactions on Biomedical Engineering, 46 (2) 148-147 (1999).
International Search Report and Written Opinion for the Application No. PCT/US2017/015601, dated May 16, 2017, 12 pages.
International Search Report and Written Opinion for the Application No. PCT/US2018/018901, dated Aug. 6, 2018, 12 pages.
International Search Report and Written Opinion for Application No. PCT/US2018/052467, dated Jan. 4, 2019, 13 pages.
"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.
"Read NFC Tags with an iPHone App on iOS 11", GoToTags, Sep. 11, 2017, web <https://gototags.com/blog/read-nfc-tags-with-an-iphone-app-on-ios-11/>.(Year:2017).
International Search Report and Written Opinion for International Application No. PCT/US2016/063350, dated Mar. 27, 2017, 9 pages.
Extended Search Report dated Aug. 13, 2018, issued in European Patent Application No. 16753053.4, 9 pages.
PCT International Search Report and Written Opinion dated Apr. 29, 2015, received in corresponding PCT Application No. PCT/US16/18452, 9 pages.
International Preliminary Report on Patentability dated Aug. 31, 2017, issued in PCT Patent Application No. PCT/US2016/018452, 7 pages.
International Search Report and Written Opinion for the International Patent Application No. PCT/US2019/055862, dated Mar. 11, 2020.

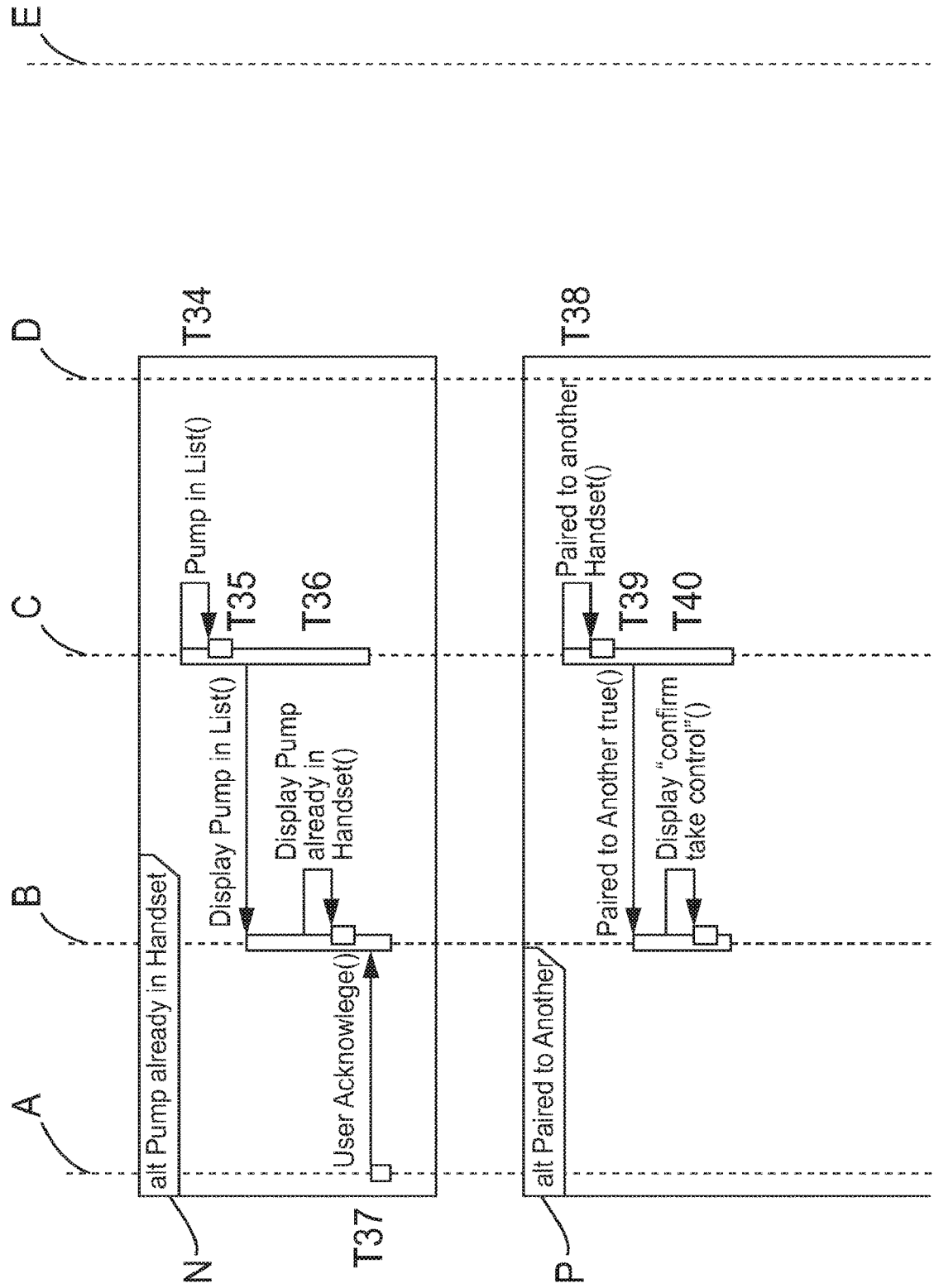
Figure 6
(Continued on sheet 4)

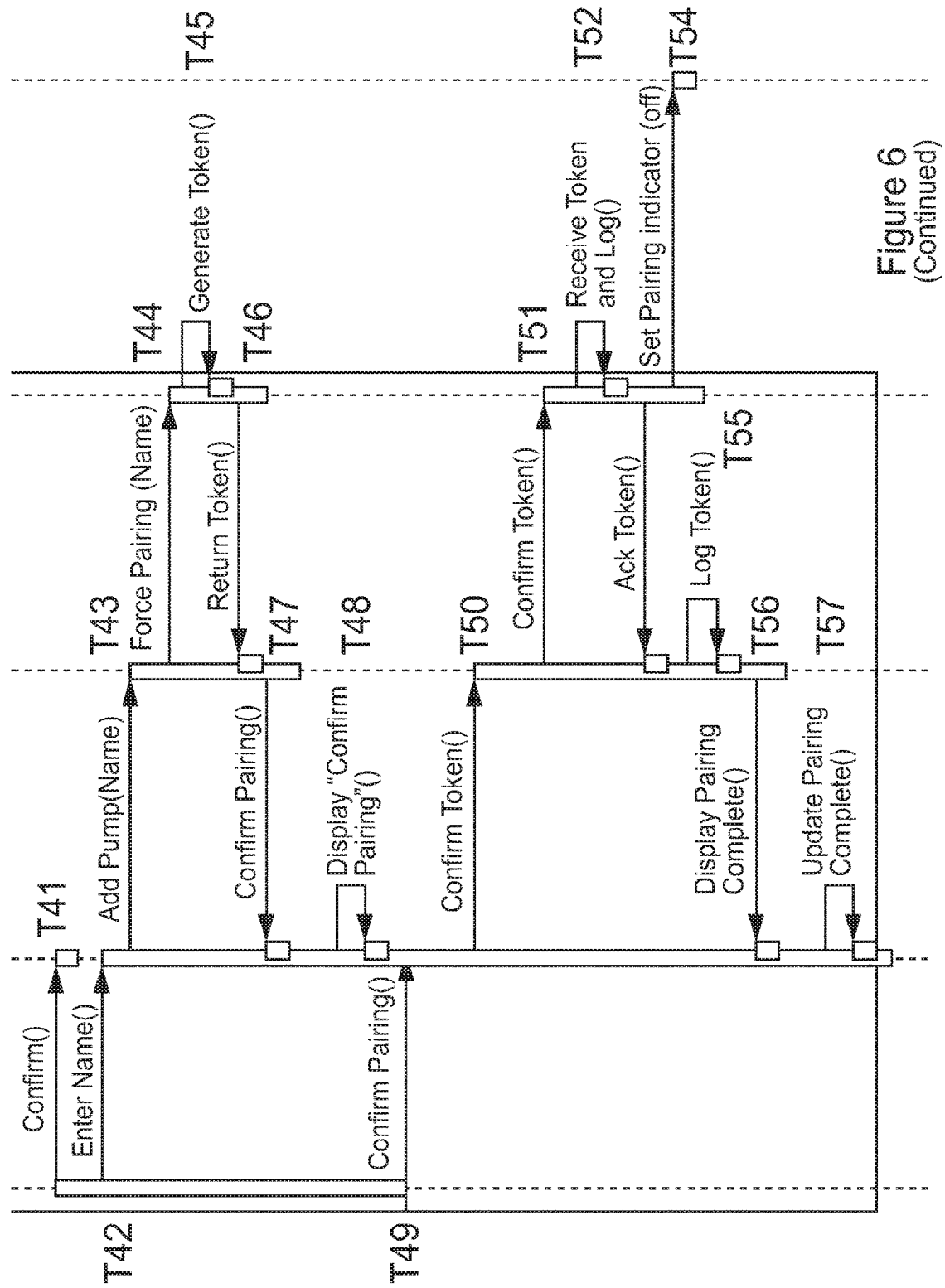

THERAPEUTIC PRODUCT DELIVERY SYSTEM AND METHOD OF PAIRING

CROSS REFERENCE TO RELATED APPLICATIONS

This Continuation application claims the benefit of U.S. application Ser. No. 15/114,843, filed on Jul. 27, 2016, of the same title, recently allowed, which application claims the benefit of United States National Stage entry under 35 U.S.C. § 371 of International Application No. PCT/GB2015/050248 filed Jan. 30, 2015, designating the United States of America and published in English on Aug. 6, 2015, which in turn claims priority to Great Britain Application No. 1401591.1, filed Jan. 30, 2014, all of which are incorporated herein by reference in their entirety.

FIELD OF THE INVENTION

The present invention relates to a therapeutic product delivery system and a method of pairing a therapeutic product delivery device to a handset for controlling the operation of the therapeutic product delivery device.

BACKGROUND

Conventionally, Type 1 diabetes has been treated with daily insulin injections. However, this inevitably results in insulin levels that do not match the normal and rapid changes in blood glucose which occur in a patient throughout the day. On the one hand, insufficient insulin and high glucose levels lead to immediate symptoms and contribute to long-term complications. On the other hand, too much insulin may result in too little blood sugar leading to loss of consciousness and convulsions. As an alternative to injections, insulin pump therapy is intended to mimic the normal physiology of the healthy pancreas. Unlike multiple daily insulin injections, an insulin pump is able to provide a constant background infusion of insulin that can be adjusted according to individual need, compensating for daily activity and exercise routines. The pump may also be programmed to deliver bolus doses of insulin to address the big glucose swings in the blood that would otherwise result from eating and drinking. By mimicking the natural physiology of the pancreas, insulin pump therapy aims to maintain a constantly normal blood glucose level; avoiding the highs that are associated with meals or the lows that come from too much insulin.

It is desirable, for reasons which will be explained subsequently, for the pump to be wirelessly controlled by a handset device. The pump, as a portable and therefore battery powered device, may run out of battery power, and a second pump device may be required while the original pump is being recharged. As a result, there is a need to provide for multiple pump devices which can be controlled by a single handset device. The use of more than one rechargeable unit with a single controller delivers a requirement that the user and the handheld device are aware that they are controlling the correct pump device. One way of achieving this would be to pre-pair handsets and a set of pump devices at the point of manufacture. However, handsets and pumps may be manufactured independently, making this solution impractical.

SUMMARY

According to an aspect of the present invention, there is provided a method of pairing a therapeutic product delivery device to a handset, the handset being restricted to controlling only delivery devices which it is paired with, the method comprising the steps of:

at the delivery device, setting, in response to the delivery device being connected to a charging device, a pairing indicator indicating that the delivery device is available for pairing, and broadcasting the pairing indicator using a radio transceiver;

at the handset, discovering the delivery device based on the broadcast pairing indicator; and pairing the discovered delivery device and the handset together.

By limiting the handset to pairing with devices which are broadcasting a pairing indicator, and by limiting the setting and/or broadcast of the pairing indicator to when the delivery device is connected to a charging device, the risk of accidentally pairing the wrong delivery device (for example someone else's) to the handset is greatly reduced. Also, given the potential severity of permitting a pump delivering insulin to a patient to be controlled by another person (not the patient), it is very important to minimize the risk of a third party being able to achieved this. A manually depressed switch on the delivery device could be accidentally depressed (and then paired with another handset), or would only require a brief opportunity to access the delivery device to perform pairing. In contrast, the present invention requires the charger (an additional hardware element) to perform pairing, and the likelihood of accidental or intentional pairing is therefore greatly reduced. The delivery device is able to be paired until the delivery device is removed from the charger, until pairing has occurred, or until the expiry of a short time-out period after the delivery device is engaged with the charger, whichever happens sooner. This provides a short, well defined, opportunity for pairing, which requires the use of a dedicated charger for the delivery device.

Embodiments of the present invention are able to fulfil the requirement that a user may need to establish a pairing connection to existing pumps after a replacement handset is issued, and that a user may need to establish a pairing connection to an existing handset after a replacement delivery device has been issued.

A method has been devised for managing the pairing of an infusion pump with a specific patient's handheld controller. This is achieved through device discovery and the exchange of unique tokens generated by the pump and the controller.

The step of discovering the delivery device may comprise scanning (at the handset device) RF channels to find broadcasting pumps having their pairing indicator set to indicate that they are available for pairing.

The connection of the delivery device to the charger may be detected by the delivery device based on one or both of a physical connection and an electrical connection between the delivery device and the charger.

The method may further comprise a step of setting, at the delivery device, a pairing indicator to indicate that the delivery device is not available for pairing when the delivery device has been paired to the handset. This prevents the delivery device from being paired to another handset once it has been paired.

The handset may be responsive to a user input to activate a delivery device currently paired to the handset, the handset being permitted to interrogate the status of any delivery device to which it is paired, but permitted to trigger the delivery of a therapeutic product only from an activated delivery device to which it is paired. Preferably, only one of the delivery devices paired to the handset can be in an activate state at any given time. In other words, there can be a plurality of delivery devices paired to a particular handset, but only one of these can be active and capable of receiving insulin delivery instructions from the handset. The user input may be the selection of a delivery device for activation from a displayed list of delivery devices which are currently paired to the handset.

The pairing step may comprise the generation of a token which is to accompany messages being communicated between the delivery device and the handset.

On activation, an encryption key may be generated for encrypting medical data before communicating it between the delivery device and the handset. The medical data to be encrypted may comprise one or more of a basal delivery rate over a period of time and a timing and dosage of bolus doses over a period of time. In other words, historical dosage information indicating the patters of insulin delivery over, for example, a whole day, are encrypted to protect the privacy of the patient's medical data. However, some status information regarding the delivery device is communicated in an unencrypted form, for example information which is not directly relevant to the patient's condition, but is instead relevant to the current operation of the delivery device. For example, the status information communicated in an unencrypted form may comprise one or more of an indication of a remaining quantity of the therapeutic product in the delivery device, a current battery charge level of the delivery device, a current basal delivery rate being administered by the delivery device, a bolus dosage currently being administered by the delivery device, or an alarm signal.

The method may comprise a step of communicating, from a discovered delivery device to the handset, an indication of whether the delivery device is unpaired, already paired to the handset, or paired to another handset.

The method may further comprise a step of fitting a protective cap onto the delivery device, the protective cap covering the electrical charging contacts of the delivery device, wherein in response to the protective cap being fitted to the delivery device, the delivery device turns off its radio transceiver. This reduces power consumption while, for example, the delivery device is not being used and is in transit.

According to another aspect of the present invention, there is provided a therapeutic product delivery system comprising a therapeutic product delivery device to be worn by a patient, and a handset device for controlling the operation of the delivery device, the handset device being operable to control only delivery devices which are paired to the handset device, wherein the delivery device comprises a controller, for setting, in response to the delivery device being connected to a charging device, a pairing indicator indicating that the delivery device is available for pairing; and a radio transceiver for broadcasting the pairing indicator;

the handset comprises a transceiver, for discovering the delivery device based on the broadcast pairing indicator; and a controller, operable in combination with the controller of the discovered delivery device to pair the discovered delivery device and the handset together.

Note that the various features of the present invention described above may be practiced alone or in combination. These and other features of the present invention will be described in more detail below in the detailed description of the invention and in conjunction with the following figures.

BRIEF DESCRIPTION OF THE DRAWINGS

In order that the present invention may be more clearly ascertained, some embodiments will now be described, by way of example, with reference to the accompanying drawings, in which:

FIG. 6 schematically illustrates a detailed action and message flow between a user, a user interface and application of a handset, a pump and a charger.

DETAILED DESCRIPTION

The present invention will now be described in detail with reference to several embodiments thereof as illustrated in the accompanying drawings. In the following description, numerous specific details are set forth in order to provide a thorough understanding of embodiments of the present invention. It will be apparent, however, to one skilled in the art, that embodiments may be practiced without some or all of these specific details. In other instances, well known process steps and/or structures have not been described in detail in order to not unnecessarily obscure the present invention. The features and advantages of embodiments may be better understood with reference to the drawings and discussions that follow.

Aspects, features and advantages of exemplary embodiments of the present invention will become better understood with regard to the following description in connection with the accompanying drawing(s). It should be apparent to those skilled in the art that the described embodiments of the present invention provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present invention as defined herein and equivalents thereto. Hence, use of absolute and/or sequential terms, such as, for example, "will," "will not," "shall," "shall not," "must," "must not," "first," "initially," "next," "subsequently," "before," "after," "lastly," and "finally," are not meant to limit the scope of the present invention as the embodiments disclosed herein are merely exemplary.

System

Figure 1:
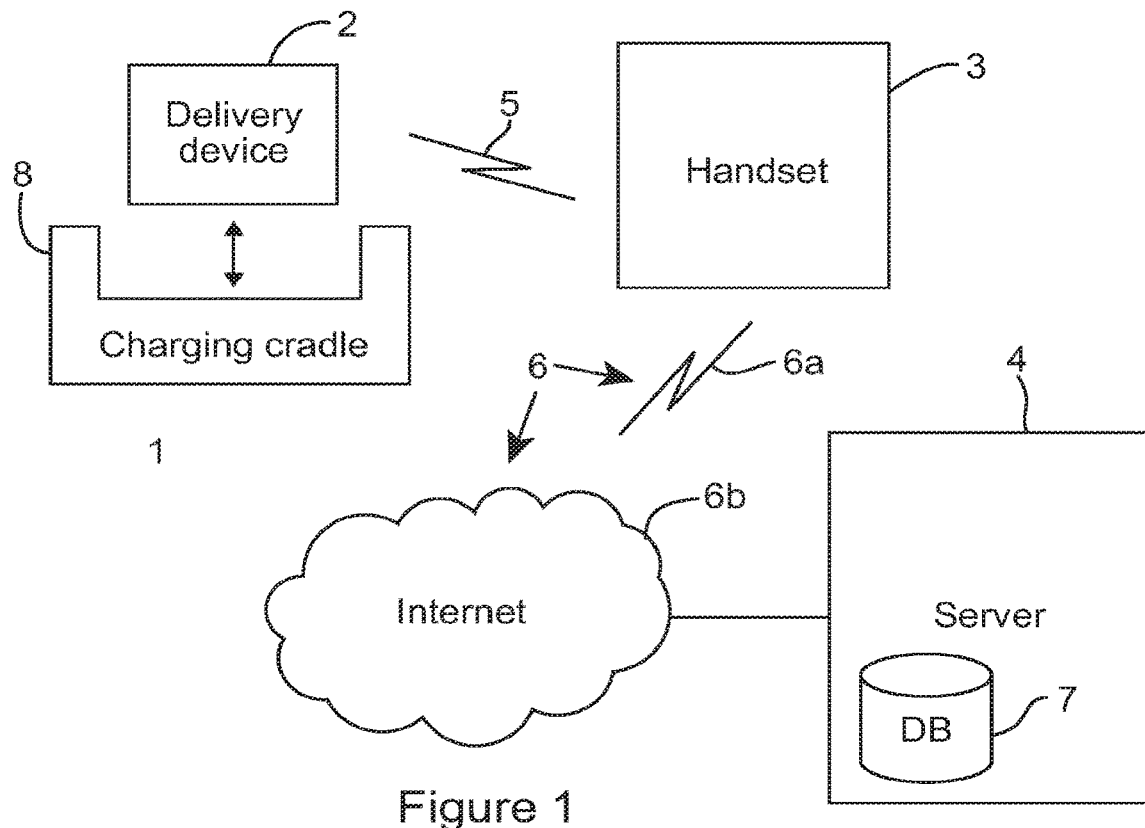
FIG. 1 shows a schematic view of a drug delivery system.

Referring to FIG. 1, a drug delivery system 1 is schematically illustrated. The drug delivery system 1 in this case delivers insulin to a patient. However, it will be appreciated that embodiments of the present invention may be appropriate for delivering drugs other than insulin. The system 1 comprises a delivery device 2 which is worn on the patient's body, a handset 3 (which may appear similar to a smartphone) for controlling the delivery device 2, and a server 4. The delivery device 2 and the handset 3 are able to communicate via a first wireless connection 5, for example a lower power ANT radio connection. The handset 3 and the server 4 are able to communicate via a second wireless connection 6, for example a GPRS mobile data connection 6a and the Internet 6b. The server 4 comprises a patient database 7 for storing patient medical information and other information about the patient. Both the delivery device 2 and the handset 3 are powered by rechargeable batteries. Also shown in FIG. 1 is a charging cradle 8 into which the delivery device 2 is inserted in order to charge the delivery device 2.

Delivery Device

Figure 2:
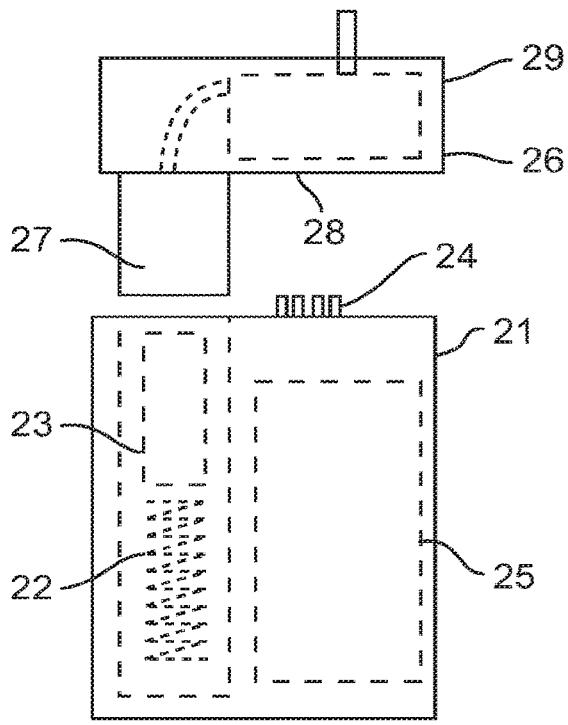
FIG. 2 shows a schematic view of a drug delivery device.
Figure 3:
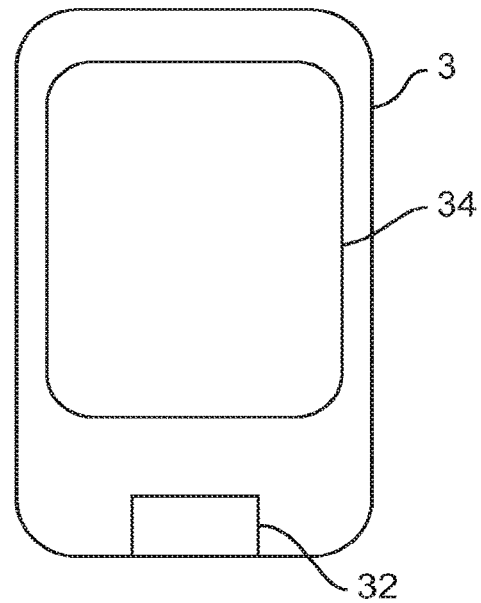
FIG. 3 shows a schematic view of a handset for controlling the drug delivery device of FIG. 2.

The delivery device comprises two parts, which are detachable from each other, as shown schematically in FIG. 2. The first of the two parts is a body 21, which contains a spring 22, a biasing member 23 including a displacement sensor (for example as described in US2011/0316562), and a set of contact pins 24 for providing an electrical connection with the second part. The body 21 also comprises a battery, control circuitry and a transceiver for communicating with the handset, which are not separately shown in FIG. 2 in the interests of clarity, but are generally represented by element 25. The second of the two parts is a disposable insulin cartridge 26, which comprises a reservoir 27 of insulin, contact pads 28 for providing an electrical connection with the body 21 via the pins 24, a pumping device (a wax actuator, for example as described in GB2443261) for pumping the insulin from the reservoir 27 into the patient's body, and a valve arrangement (for example as described in US2010/0137784). The pumping device and valve arrangement are not separately shown in FIG. 2 in the interests of clarity, but are generally represented by element 29. It will be understood that the body 21 of the delivery device is reusable, while the disposable cartridge 26 is intended to be removed and disposed of when the reservoir 27 has been depleted, or when the cartridge has passed its use by date, or if it develops a fault. A new cartridge can then be engaged with the body 21. While it is preferable that the cartridge is disposable, it will be appreciated that, in principle, the cartridge may be refilled and reused again rather than being disposed of. However, even in this case the cartridge should be removable from the body so that a new (full) cartridge can be used while the original cartridge is being refilled.

In use, the body 21 and the cartridge 26 of the delivery device 2 are physically and electrically connected. The electrical connection is via the pins 24 and pads 28. The physical connection may be provided by clips or any other releasable engagement mechanism (not shown). The control circuitry in the body 21 is responsive to control signals received from the handset 3 via the wireless connection 5 to draw current from the battery and apply an electrical current via the pins 24 and the pads 28 to activate the pumping device within the cartridge 26 to draw fluid from the reservoir 27 through the valve arrangement and out of the delivery device 2 to a patient's body. The rate of delivery of the therapeutic product can be controlled by the control circuitry to achieve a particular basal delivery rate, or bolus dose, by controlling the amount and timing of electrical current to the pumping device. Although the basal rate is set by the handset, once set the delivery device 2 is able to maintain the set basal rate with no further communication from the handset 3. As can be seen in FIG. 2, when the body 21 and the cartridge 26 are in engagement, the reservoir 27 is received within the body 21, displacing the biasing member (and displacement sensor) 23 and compressing the spring 22. The compressed spring applies a biasing force to a base of the reservoir 27 via the biasing member 23. The biasing force does not in isolation force insulin from the reservoir 27 through the valve arrangement and into the patient's body, but when combined with the pumping action of the pumping device, the biasing force pressurizes the insulin in the reservoir 27 to refill a pumping chamber in advance of each pumping action. It is the pumping action which drives a controlled amount of insulin from the pumping chamber through an outlet valve and to the patient's body. The reservoir takes the form of a cylinder having a first end from which insulin is drawn under the action of the pump, and a second end opposite to the first end at which the (moveable) base is provided. The base of the reservoir moves inwardly of the reservoir (to effectively decrease the size of the reservoir) as the insulin is pumped from the reservoir, under the biasing force provided by the biasing member 23. The position of the biasing member 23 is dependent on the current fill state of the reservoir—that is, how much insulin is remaining in the reservoir. The position of the biasing member 23, and thus the base of the reservoir 27, is determined by the displacement sensor. The displacement sensor is therefore able to generate a signal indicative of the remaining quantity of insulin in the reservoir. By monitoring the change in the remaining quantity of insulin with respect to time, an actual rate of insulin delivery can be determined. This can be used by the control circuitry to apply corrections to the actual delivery rate by adapting the amount and/or timing of electrical current to the pumping device. The quantity of insulin remaining in the reservoir is transmitted to the handset 3, where it can be displayed to the patient and used as an indicator of when the patient should change the current cartridge for a new cartridge. The control circuitry in the body 21 may also transmit an indication of current battery level to the handset, so that the patient is made aware of when the battery requires recharging.

The delivery device also contains an activity monitor to track exercise (not shown). Exercise can have a significant effect on the amount of insulin needed for good control, so tracking exercise accurately is an important part of effective diabetes management. The activity monitor uses a sensor in the delivery device to detect movement of the delivery device, which can be used to infer when the user is engaged in physical activity. The detected activity is then wirelessly communicated to the handset via the wireless connection 5, where the handset (and the server) is able to track and record the patient's activity. Through an online portal to the server, the patient and permitted medical professionals are able to compare activity peaks with blood glucose to identify how activity is influencing the patient's need for insulin. This can in turn be used to program the handset with appropriate dosages for the patient.

Due to the fact that the patient interfaces with the handset rather than the delivery device itself, the delivery device is able to be made small and discreet, and is provided without buttons or a physical connection to a control unit.

Handset

The handset 3 comprises two transceivers. The first transceiver is for communicating with the delivery device via the first wireless connection 5, while the second transceiver is for communicating with the server 4 via the second wireless connection 6. The handset also comprises a processor for running control software. The control software monitors the patient's condition and reports it to the central server 4, and controls the delivery of insulin doses to the patient by transmitting control signals to the delivery device 2. The handset 3 also comprises a touch screen display 34, which displays information to the user and provides a user interface for the user to input data, modify the basal rate, and trigger extraordinary bolas doses.

As well as wirelessly controlling the pump, the handset 3 also has an integral blood glucose meter 32. The blood glucose meter 32 detects the amount of glucose in the patient's blood. The blood may be analyzed at the meter 32 by pricking the patient's finger and depositing a droplet of blood on a slide, which is inserted into the meter 32. The detected blood glucose level can be brought to the attention of the patient on the handset 3, and the patient can decide to trigger a bolas dose based on the blood glucose information. The result of every blood glucose test is automatically logged by the software and becomes immediately available for reference via the server 4 to the patient, medical professionals and even family members (such as parents). More generally, the handset 3 runs various software applications which help the user (and other authorized parties) to keep track of diet, insulin, blood glucose and exercise (which as explained above is recorded automatically from a sensor in the delivery device). By automating data collection, the handset 3 eliminates, or at least reduces, the need for a diabetes journal and ensures that comprehensive and accurate clinical information are constantly available to the patient and medical professionals via the server 4.

When controlling the delivery device, the handset 3 sends wireless signals to the delivery device 2 to deliver regular periodic doses of insulin at a pre-determined basal rate, which is set on the handset 3 according to the recommendations of a medical professional. The basal rate may be adjustable by the user within certain constraints. However, the software is configured such that it is not allowed for the basal rate to be adjusted remotely by third parties such as doctors. The hand-held device 3 also allows the user to trigger extraordinary bolus doses, for example after eating carbohydrates or performing exercise. As with a basal dose, the bolus dose is delivered by the delivery device 2 in response to control signals sent wirelessly from the handset 3. The user is able to input the volume of carbohydrates which have been consumed at a relevant time and is also able to input periods of exercise and the hand-held device is able to recommend adjustments to the basal rate or when a bolus is needed. As discussed above, the glucose monitor 32 may have an influence on the dosage. All of this information is transmitted to the server 4. The hand-held device 3 also receives information from the delivery device 2, for example to indicate whether it is faulty or when the insulin cartridge needs to be replaced. It also provides an indication of battery level.

Server

It will be understood from the above that the handset 3 and the delivery device 2 monitor and record clinical information while delivering insulin according to the body's needs. By providing this information to the server 4, it can be made almost immediately available to all those who need to see it. In particular, a mobile connection to a secure online management portal makes it possible for patients, clinicians and parents to be made constantly aware of, and able to react to, changing conditions. A diabetes clinic with patients using the system is able to see the current status of all its patients on a single screen, delivered to the clinic in real time. The portal can be accessed over the Internet in the clinic or through a smartphone. In addition to making it possible for a patient to access their latest clinical information online, it is possible for the patient to see simple visual analysis of their data, for example to identify trends and patterns in their blood sugar, and to immediately see their insulin dosing habits. This information can all be viewed using a simple online web portal that can be accessed from home, from work or from a smartphone. The server can also transmit SMS messages to a child's parents to let them know their child's information and state of health.

A patient using the system is provided with a personal login to the secure mobile diabetes management portal. Once logged in the patient can see all of their automatically collected data in the form of charts and graphs to help them understand where they might need to make adjustments. Exercise habits are mapped out in pie charts. An indication of exactly how and when the patient's insulin was delivered is provided. The patient's clinicians are able to see the same analysis and information, enabling them to call or text the patient whenever needed with guidance and advice.

From a single online dashboard screen, the clinic has access to the status of all the patients on the system; including current blood sugar, average blood sugar, insulin dosing, hypo frequency and blood testing habits. At a glance, anyone having difficulties can easily be identified for an immediate response. With a single click, all the data for a patient is analyzed and charted to identify trends, patterns and problems. Using the portal, clinics can completely reorganize the way in which patients are managed. Text and email can be used to check on recent events. Clinic visits are focused completely on current and accurate information.

Pairing of the Handset and the Delivery Device

A user can be expected to have more than one delivery device (pump), for example so that one can be used whilst the other is charging. The user may sometimes need to pair a new pump with his handset (for example because he has received a new pump, or a new handset) and, in order to avoid the risk of accidently pairing with the wrong pump or someone else's pump, pairing can only take place whilst the relevant pump is connected to its charger. This connection can either be a mechanical connection, for example having a pin on the charger which depresses an actuator on the pump body (or vice versa), or electronically, for example by interconnecting two terminals. It will be appreciated that an electrical connection is inherent in any connection between a charger and a device which it is charging, and this connection may itself form the basis for the detection (the charging circuitry responsible for charging the battery of the device when the device is connected to the charger needs to be responsive to the connection to initiate charging). The person skilled in the art will be aware of a number of techniques for detecting an electrical connection between two devices, and in particular between a charger and a device to be charged. There is only the need to form pairing once. The handset is able to display a list of the pumps which it is paired with, and the user is able to select which pump to use (activate) out of the listed pumps. The handset will only control insulin delivery using an activated and paired pump, and it is only possible to have one of the paired pumps active at any given time.

Pairing (Discovery) is therefore securely tied to the charger. The Pairing process is initiated when the user places the delivery device in its charging cradle. Following the connection of the delivery device to the charger, a predetermined period (for example 5 minutes) is provided during which time pairing is possible. Following the expiry of this period pairing is no longer possible (unless the delivery device is removed from and reconnected to the charger). The delivery device recognizes when it is inserted into an authorized charger and only then will it enable discovery by handset devices by setting a pairing attribute (bit) in a broadcast from its radio transceiver. After the predetermined time, the pairing bit will be changed so that the delivery device is no longer discoverable, and can no longer be paired to a handset. The broadcast itself may be triggered by the insertion of the delivery device into the charger, or may be a regular broadcast, in which the pairing attribute is merely modified from non-discoverable to discoverable by the insertion of the delivery device into the charger. In the former case, it will be appreciated that, since the broadcast only takes place while the delivery device is connected to the charger, the additional power consumption associated with the broadcast will not drain the battery of the delivery device, because the battery will be on charge at the time.

Once the delivery device has been inserted into the charging cradle, at the handset, a software application (wizard) guides the user through the pairing process. The user selects "Search" for pumps and the handset scans the RF channels for pumps with their pairing bit set. When a pump is discovered the handset requests its pairing status details and receives these back. The handset can then determine from the pairing status details whether the pump is New, Already paired to this handset or whether the pump is paired to another handset. The latter status can arise if a replacement handset has been issued to the user. The user can then choose to pair with the pump and adds a "Tag" or name to identify the pump in its handheld list for future use. The delivery device acts as a master, controlling its discovery mode (using the pairing bit) and exchanging tokens with the handset device to create a "Master-Slave relationship". Once paired the agreed tokens are used during all communications between the slave and master to validate that the correct slave (handset) is sending the requests to the Pump. In other words, using the agreed tokens, each of the handset and the pump are able to determine whether a particular received communication (for example a command from a handset to a pump, or status information from a pump to a handset) is from a device which it is paired with. When pairing occurs, the pump will discard any token agreed with a handset to which it was previously paired, and so if a previous handset attempts to control the pump the tokens will not match and the handset will fail to exert control over the pump. This addresses the problem of a pump delivering insulin in response to a command from a handset which it is not paired with, or the handset (and consequently the server) acquiring status information about a pump which it is not paired with. This is important for a variety of reasons, including the fact that the dissemination of this information to the wrong handset (and thus user) would both infringe the privacy of a user (other than the user of the handset), and cause the wrong medical information to be associated with the user of the handset, which could cause diagnostic problems downstream. The status information may comprise activity data regarding times and amounts of delivery of insulin to the patient (both basal and bolus doses).

Figure 4:
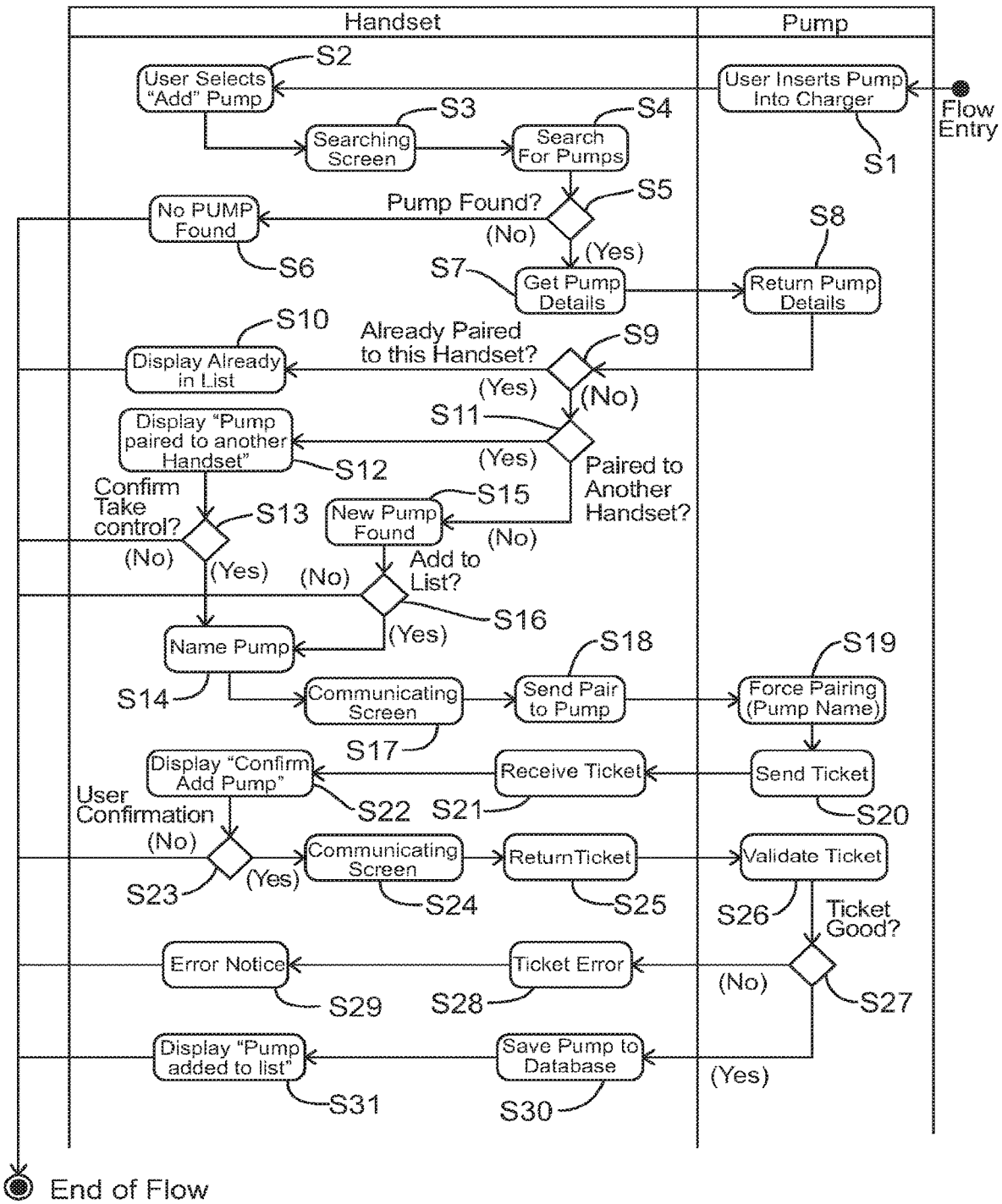
FIG. 4 schematically illustrates a pairing activity flow for the handset and pump.

Referring to FIG. 4, a pairing activity flow for the handset and pump is schematically illustrated. The left hand column of FIG. 4 contains the steps conducted by the handset, while the right hand column of FIG. 4 contains the steps conducted by the delivery device (referred to here as a pump). At a step S1, the user inserts the pump into its charger. The mechanical and/or electrical engagement between the pump and its charger causes a pairing indicator to be set to make the pump discoverable by a handset device. The pairing indicator is broadcast by a radio transceiver (preferably an ANT radio) in the pump, and is therefore received by nearby handsets. At a step S2, the user selects an "add pump" function at their handset device using the user interface. This brings up a searching screen at a step S3. At a step S4, the handset scans for broadcasts from nearby discoverable pump devices. At a step S5, it is determined whether any new pumps have been found. If not, the searching screen is updated to indicate that no new pumps have been found, and the process terminates at a step S6. If at the step S5 it is determined that one or more new pumps have been found, then at a step S7 the handset attempts to obtain pump details from each pump found. At a step S8, the pump device returns its pump details to the handset, which will include the current pairing status of the pump device (as described previously). It is then determined at a step S9 (at the handset) whether the pump device is already paired to the handset. If so, then the searching screen is updated to indicate that the found pump is already in the list of paired pumps at the handset, and the process terminates at a step S10. If at the step S9 it is determined that the found pump is not already paired to the handset, then it is determined at a step S11 whether the pump is already paired to another handset. If so, then the searching screen is updated at a step S12 to indicate that the pump is paired to another handset, and the user is given the opportunity to take control of the pump (from the other handset) at a step S13. If the user chooses not to take control, then the process ends. If the user does choose to take control of the pump, then the pump is named (for display in the list of paired pumps) at a step S14. It will be understood that it may be necessary for a pump which is paired to another handset to be unpaired from that handset (by discard an old token associated with the previous pairing, in favor of a new token associated with the new pairing, as described elsewhere), so that a user can have a replacement handset (for example because his old one becomes broken or lost) without needing to replace the pump devices too. If at the step S11 it is determined that the pump is not paired to another handset (and it thus unpaired), then at a step S15 it is determined that a new pump has been found, and the user is provided with the opportunity to add the new pump to the list of paired pumps at a step S16. If the user chooses not to add the new pump to the list, then the process ends. If the user chooses to add the new pump to the list, then the new pump is given at a name at the step S14.

Once the pump has been named, a communicating screen is displayed at the handset at a step S17. A pairing request is then sent to the pump at a step S18. In response, pairing is forced at the pump at a step S19, and the pump name is asserted. At a step S20, a ticket is communicated from the pump to the handset. At a step S21 the ticket is received at the handset, and in response the communicating screen is updated at a step S22 to request the user to confirm that the pump should be added. If the user declines at a step S23, then the process ends. If the user confirms that the pump should be added at the step S23, then the communicating screen is updated at a step S24 and the ticket is returned from the handset to the pump at a step S25. At a step S26, the ticket is validated at the pump. In particular, at a step S27 it is determined whether the ticket is valid, and if not then at a step S28 a ticket error is communicated to the handset, and used to generate an error notice, whereupon the process ends. If at the step S27 it is determined that the ticket is valid, then the pump is saved to the database (at the handset) at a step S30, and the communicating screen is updated to indicate to the user that the pump has been added to the list of available pumps.

Figure 5:
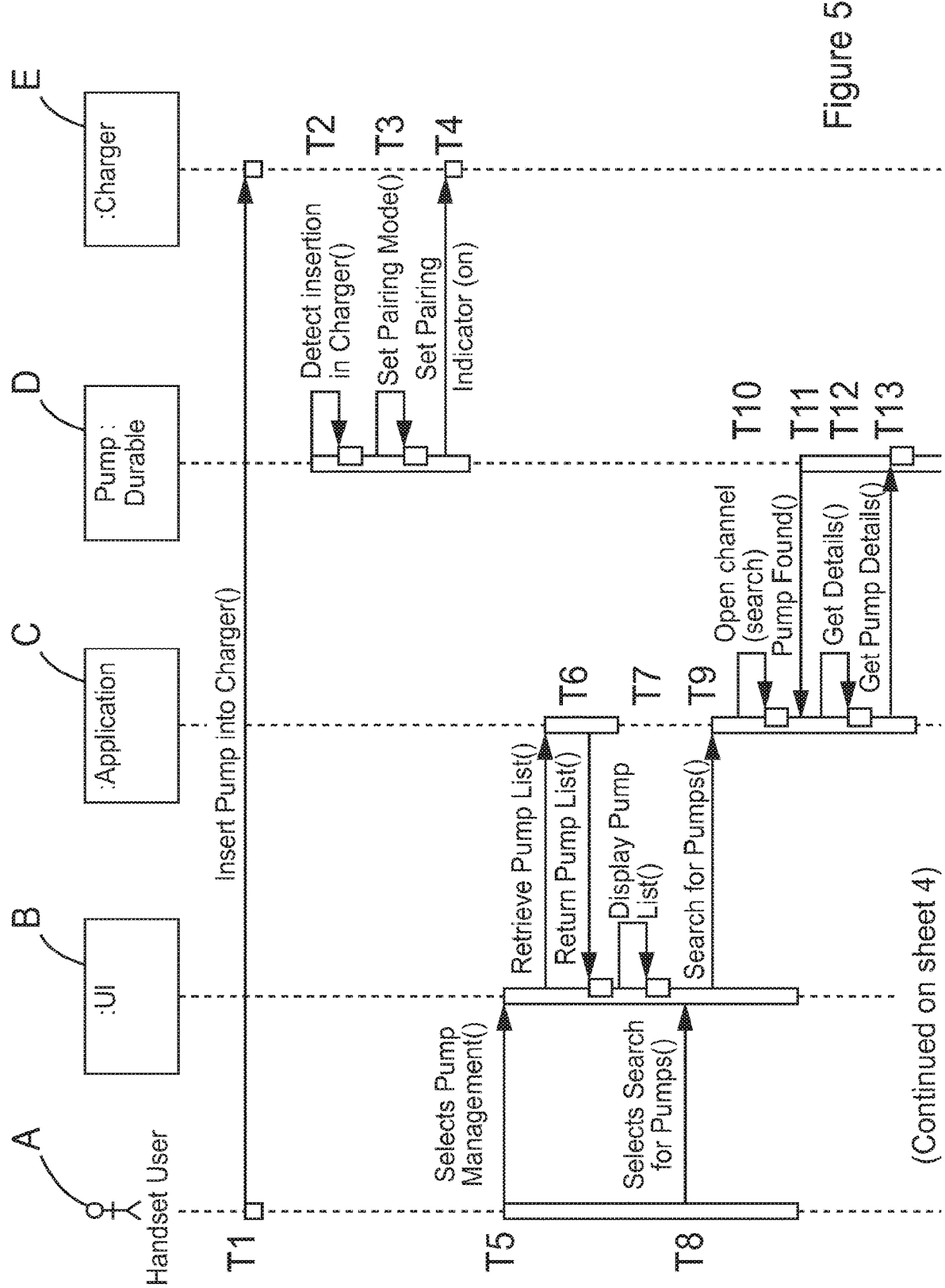
FIG. 5 schematically illustrates a detailed action and message flow between a user, a user interface and application of a handset, a pump and a charger.
Figure 5:
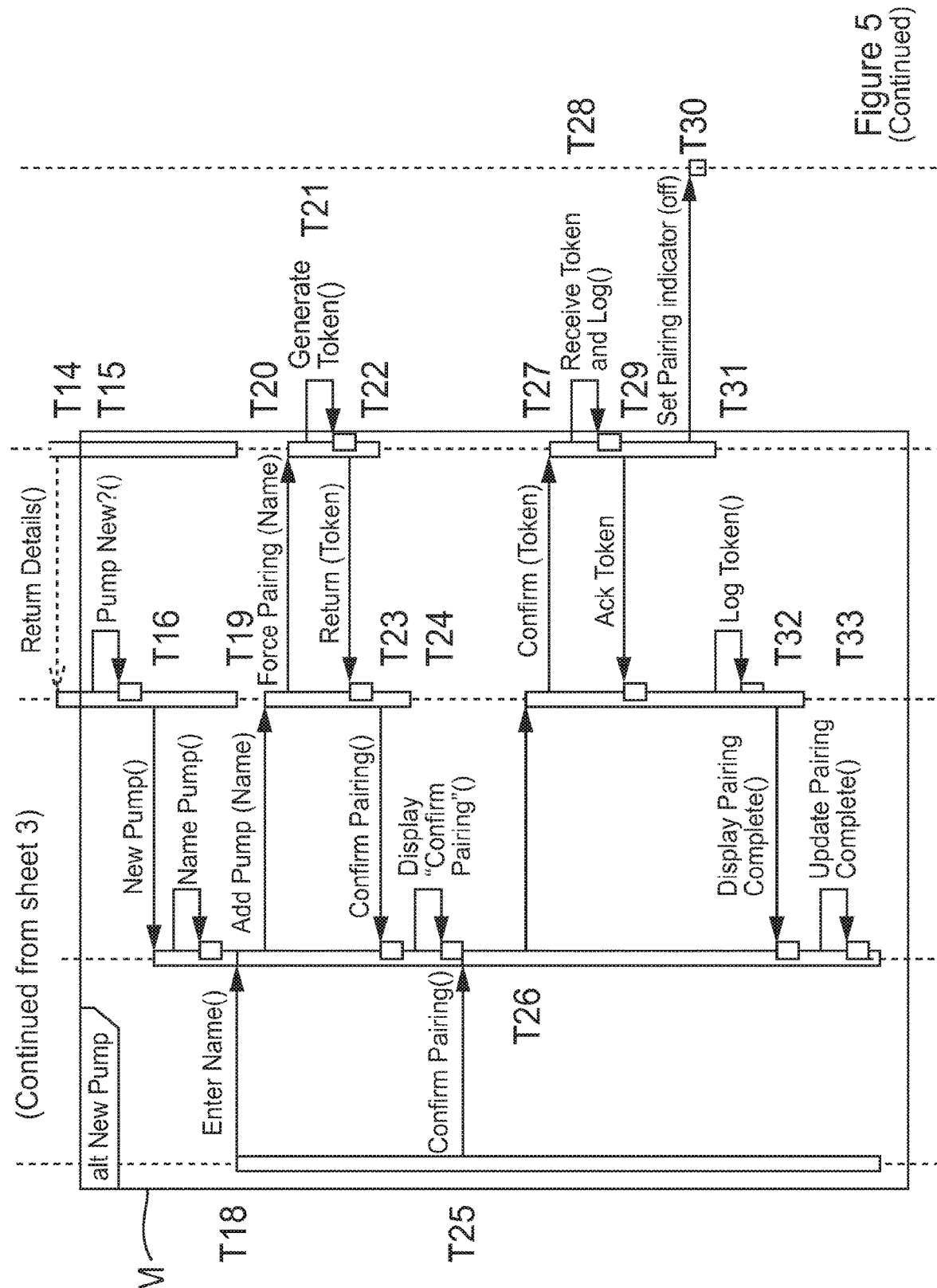

Referring now to FIG. 5, this schematically illustrates a detailed action and message flow between a user A, a user interface B and application C of a handset, a pump D and a charger E. The process is described with respect to time from a first step T1 through to a step T33. At the step T1, the user A inserts the pump D into the charger E. In response to this, the pump D detects its insertion in the charger E at a step T2. Then, at a step T3 the pump D is set into a pairing mode, and a pairing indicator (pairing=on) is set and broadcast at a step T4. The broadcast pairing indicator can be received by any handset device within range, making the pump D discoverable to those handsets. At a step T5 the user A selects a pump management function at the user interface B of the handset. At a step T6, the user interface B requests the application C to retrieve and return a list of currently paired pumps to the user interface B for display to the user A at a step T7. At a step T8, the user A observes that the desired pump is not on the pump list and is not currently paired, and therefore selects a search for pumps function on the user interface B. At a step T9 the user interface B requests the application C to search for discoverable pumps using a radio transceiver of the handset. At a step T10 the application C opens a radio channel to search for discoverable pumps. At a step T11, the pump D is found. At a step T12 the application C attempts to obtain details for the discovered pump, and therefore transmits a GetPumpDetails message to the pump D at a step T13. At a step T14, the pump details are returned from the pump D to the application C.

The situation in case the pump D is a new pump is covered by the message flow set out in box M. In particular, at a step T15 it is determined by the application C that the found pump is a new pump (that is, not currently listed on the pump list). In this case, at a step T16 a new pump message is provided to the user interface B, and the user is offered the opportunity, at a step T17, to input a name for the pump. At a step T18 the user A enters the name, and at a step T19 the user interface B passes an instruction to the application C to add the pump (with its name) to the list of available (paired) pumps. At a step T20 the application C sends a force pairing message to the pump D, in response to which the pump D generates a token at a step T21 and sends it back to the application at a step T22. A confirm pairing message is then provided by the application C to the user interface B, triggering the user interface B to display a confirm pairing message to the user A. In response to this, the user A is able to confirm the pairing at a step T25, resulting in the transmission of a confirm token from the user interface B to the application C at a step T26, which is forwarded on to the pump D at a step T27. The pump D receives and logs the token at a step T28, and send back an acknowledgement token to the application C at a step T29. Also, the pairing indicator for the pump D is set to off at a step T30 to prevent the pump D from being paired to another handset. As a result, the pump D will no longer be discoverable. The acknowledgement token is then logged at the application C at a step T31, and a message is sent to the user interface B at a step T32 to display a pairing complete message on the handset. At a step T33, the pairing process is completed.

Referring now to FIG. 6, this schematically illustrates a detailed action and message flow between the user A, the user interface B and application C of a handset, the pump D and the charger E. The messages in box N relate to the process where a discovered pump (through the steps T1 to T14 of FIG. 5) is already in the list of paired pumps at the handset. In this case, at a step T34 (following the step T14) it is determined at the application C that the pump D is already in the list of paired pumps. The application C therefore sends a display pump in list message to the user interface B at a step T35, which causes the user interface B to display a pump already paired with handset message at a step T36, which the user A acknowledges at a step T37.

The messages in box P relate to the process where a discovered pump (through the steps T1 to T14 of FIG. 5) is already paired to another handset. In this case, it is still possible to pair the pump with a new handset (it will be appreciated that the risk of a handset misappropriating access to another person's handset is substantially reduced by limiting pairing to when a pump is connected to a charger). In particular, at a step T38 (following the step T14) it is determined at the application C that the pump D is paired to another handset. A paired to another handset message is therefore sent from the application C to the user interface B at a step T39, causing it to display a message at a step ST40 to the user A asking the user A if they would like the handset to take control of the pump D anyway. At a step T41 the user A confirms this desire, and at a step T42 enters a name for the pump. Steps T43 to T57 are then conducted, which are identical to the steps T19 to T33 and therefore will not be repeated.

The process of FIGS. 4 to 6 describe how therapeutic product delivery devices can be paired with a handset. It is not possible for a single delivery device to be paired with multiple handsets, because the delivery device will effectively be unpaired from a previous handset when it pairs with a new handset (by agreeing a new token to accompany communications between handset and pump). Moreover, it is not possible for a single handset to simultaneous instruct multiple devices to administer a therapeutic product, because following pairing it is necessary for the handset to activate a device before being able to instruct it to administer the therapeutic product, and only a single device is permitted to be activated at any given time. In order to activate a delivery device, the user will typically select a device to activate from a list of currently paired pumps displayed on the handset. While the handset is able to access information about each of the paired pumps (such as current insulin fill level and battery charge level), it is only able to control the delivery of a therapeutic product to an activated pump to which it is paired. On activation, an encryption key may be generated for encrypting medical data before communicating it between the delivery device and the handset. The encryption key may be an XTEA encryption key for example. Encryption keys may be generated and swapped between the handset and the delivery device by using known techniques, for example by using secret/network key encryption or public/private key encryption. The medical data to be encrypted may comprise one or more of a basal delivery rate over a period of time and a timing and dosage of bolus doses over a period of time. In other words, historical dosage information indicating the patterns of insulin delivery over, for example, a whole day, are encrypted to protect the privacy of the patient's medical data. However, some status information regarding the delivery device is communicated in an unencrypted form, for example information which is not directly relevant to the patient's condition, but is instead relevant to the current operation of the delivery device. For example, the status information communicated in an unencrypted form may comprise one or more of an indication of a remaining quantity of the therapeutic product in the delivery device, a current battery charge level of the delivery device, a current basal delivery rate being administered by the delivery device, a bolus dosage currently being administered by the delivery device, or an alarm signal ((for example to indicate that the pump is low on battery power, that the insulin reservoir is depleted, or that the pump (main body or cartridge) has developed a fault). The delivery device does not need to be connected to the charger in order for it to be activated by the handset. It need only be already paired with the handset.

The delivery device may transmit a broadcast on a regular basis (for example 2 broadcasts per second), irrespective of whether the delivery device is currently paired to a handset, activated, or neither, and irrespective of whether the delivery device is currently sat in a charging cradle. However, in some cases the content of the broadcast may differ depending on whether the delivery device is unpaired, paired but not active or paired and active. In the example embodiment, the two part delivery device is such that the disposable cartridge must be removed in order to insert the main body into the charging cradle (because the same contact pins are used both for providing the electrical connection with the disposable cartridge, and also with the charger). In the case of a broadcast from a delivery device which is currently inserted in the cradle, this may include an identifier for the delivery device and the pairing bit (set to permit discovery/pairing for 5 minutes, or until pairing to a handset is completed, and set not to permit discovery/pairing after this), to indicate whether it is currently possible for a handset to pair with the delivery device. When the delivery device is paired, removed from the charging cradle and the cartridge is fitted, the broadcast may include the identifier and basic status information indicating a current battery level and reservoir fill state for the delivery device. In the case of a paired and active delivery device, the broadcast may include flags indicating the occurrence of an event (e.g. bolus dose administered) at the delivery device or an alarm condition on the delivery device (e.g. battery low, reservoir low or device fault), or indicating the presence of a log/history which is available for transmission from the delivery device to the handset (and then on to the server). The handset is then made aware, via the flags, of information (e.g. an event or history) it may be interested in, and can then send a request status message to the delivery device to request the delivery device to provide more detailed information. The more detailed information could be provided in the form of a file. In the case of an event that a bolus dose has been administered the file might indicate the actual bolus dose administered to the patient. In the case of a history, the file might set out a list of times (start and stop times) and amounts of insulin delivered to the patient, both as regular (basal) doses and bolus doses, and also information from the activity monitor regarding the amount the patient has moved around. It will be appreciated that, if improved timeliness is necessary for e.g. the alarm conditions, then a dedicated alarm message could be sent in addition to the usual broadcast message. This would also have the advantage of improved reliability, since it is less likely that two messages (dedicated+broadcast) would be lost than a single message.

Also provided may be protective cap which can be fitted onto the delivery device, preferably over the electric contacts to prevent these being damages, becoming wet or becoming clogged with debris. When the protective cap is fitted to the delivery device, the delivery device turns off its radio transceiver. This reduces power consumption while, for example, the delivery device is not being used and is in transit, without the user needing to take an explicit action to turn off the delivery device. It will be appreciated that it is desirable for the default position to be for the delivery device to regularly broadcast its presence to enable a handset device to take control of it readily. However, the user would not need to take control of a delivery device which is fitted with the protective cap for travel purposes.

While embodiments of the present invention have been described with reference to an insulin delivery system, it will be appreciated that the present invention may be applied instead to the delivery of other drugs.

While this invention has been described in terms of several embodiments, there are alterations, modifications, permutations, and substitute equivalents, which fall within the scope of this invention. Although sub-section titles have been provided to aid in the description of the invention, these titles are merely illustrative and are not intended to limit the scope of the present invention.

It should also be noted that there are many alternative ways of implementing the methods and apparatuses of the present invention. It is therefore intended that the following appended claims be interpreted as including all such alterations, modifications, permutations, and substitute equivalents as fall within the true spirit and scope of the present invention.

What is claimed is:

1. A method of pairing a therapeutic product delivery device to a handset, the method comprising:
    at the delivery device, setting, in response to the delivery device being connected to a charging device, a pairing indicator indicating that the delivery device is available for pairing, and broadcasting the pairing indicator;
    at the handset, discovering the delivery device based on the pairing indicator; and
    communicating, from the delivery device to the handset, an indication of whether the delivery device is unpaired, already paired to the handset, or paired to another handset.

2. A method according to claim 1, wherein discovering the delivery device comprises scanning RF channels to find broadcasting pumps having their pairing indicator set to indicate that they are available for pairing.

3. A method according to claim 1, wherein the connection of the delivery device to the charger is detected based on one or both of a physical connection and an electrical connection between the delivery device and the charger.

4. A method according to claim 1, further comprising a step of setting, at the delivery device, a pairing indicator to indicate that the delivery device is not available for pairing when the delivery device has been paired to the handset.

5. A method according claim 1, wherein the handset is responsive to a user input to activate a delivery device currently paired to the handset, the handset being permitted to interrogate the status of any of a plurality of delivery device to which it is paired, but permitted to trigger the delivery of a therapeutic product only from an activated delivery device to which it is paired.

6. A method according to claim 5, wherein only one of the plurality of delivery devices paired to the handset can be in an activate state at any given time.

7. A method according to claim 5, wherein the user input is the selection of a delivery device for activation from a displayed list of the plurality of delivery devices which are currently paired to the handset.

8. A method according claim 1, further comprising pairing the delivery device and the handset together when the delivery device is indicated to be unpaired or paired to another handset.

9. A method according to claim 1, wherein on activation, an encryption key is generated for encrypting medical data before communicating it between the delivery device and the handset.

10. A method according to claim 9, wherein the medical data to be encrypted comprises one or more of a basal delivery rate over a period of time and a timing and dosage of bolus doses over a period of time.

11. A method according to claim 9, wherein some status information regarding the delivery device is communicated in an unencrypted form.

12. A method according to claim 11, wherein the status information communicated in an unencrypted form comprises one or more of an indication of a remaining quantity of the therapeutic product in the delivery device, a current battery charge level of the delivery device, a current basal delivery rate being administered by the delivery device, a bolus dosage currently being administered by the delivery device, or an alarm signal.

13. A method according claim 1, further comprising a step of fitting a protective cap onto the delivery device, the protective cap covering the electrical charging contacts of the delivery device, wherein in response to the protective cap being fitted to the delivery device, the delivery device turns off its radio transceiver.

14. A system, comprising:
a therapeutic product delivery device to be worn by a patient;
a handset device for controlling operation of the therapeutic product delivery device, the handset device being operable to control the therapeutic product delivery device only when the therapeutic product delivery devices is paired to the handset device, wherein the therapeutic product delivery device comprises a controller, for setting, in response to the therapeutic product delivery device being connected to a charging device, a pairing indicator indicating that the therapeutic product delivery device is available for pairing, and
wherein the handset is operable to discovering the therapeutic product delivery device based on the pairing indicator; and
a processor, operable in combination with the controller of the therapeutic product delivery device to pair the therapeutic product delivery device and the handset together.

15. A computer program embodied in non-transitory computer-readable medium, which when executed on a data processing device causes the data processing device to perform the steps of claim 1.

* * * * *